(12) United States Patent
Kitamura et al.

(10) Patent No.: US 7,974,669 B2
(45) Date of Patent: Jul. 5, 2011

(54) METHOD FOR MEASURING GLUCOSE CONCENTRATION IN BLOOD USING INFRARED SPECTROSCOPY AND INSTRUMENT EMPLOYING IT

(75) Inventors: Akihide Kitamura, Chiba (JP); Fumio Nomura, Chiba (JP); Takashi Karatsu, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 11/572,960

(22) PCT Filed: Jul. 26, 2005

(86) PCT No.: PCT/JP2005/013660
§ 371 (c)(1),
(2), (4) Date: Jan. 30, 2007

(87) PCT Pub. No.: WO2006/011487
PCT Pub. Date: Feb. 2, 2006

(65) Prior Publication Data
US 2009/0004682 A1    Jan. 1, 2009

(30) Foreign Application Priority Data
Jul. 30, 2004  (JP) ................................. 2004-223934

(51) Int. Cl.
*A61B 5/00* (2006.01)
(52) U.S. Cl. .................................................... 600/316
(58) Field of Classification Search .................. None
See application file for complete search history.

(56) References Cited

U.S. PATENT DOCUMENTS 6,421,548 B1 * 7/2002 Berman et al. ............... 600/322
2004/0147034 A1 * 7/2004 Gore et al. ..................... 436/95

FOREIGN PATENT DOCUMENTS

| JP | 2002-131228 A | 5/2002 |
| JP | 2003-042948 | 2/2003 |
| WO | WO 03/069308 A2 | 8/2003 |

OTHER PUBLICATIONS

Shen et al. The Use of Fourier-Transform Infrared Spectroscopy for the Quantitative Determination of Glucose Concentration in Whole Blood; Physics in Medical Biology, vol. 48 (2003) pp. 2023-2032.*
Kim et al. Determinationof Glucose in Whole Blood Samples by Mid-Infrared Spectroscopy; Applied Optics, vol. 42, No. 4 (2003) pp. 745-749.*
Karatsu et al. Determination of the Glucose in Serum by the FT-IR-ATR Method; Bunseki Kagaku, vol. 54, No. 2 (2005) pp. 149-154.*
Petibois et al. Determination of Glucose in Dried Serum Samples by Fourier-Transform Infrared Spectroscopy; Clinical Chemistry, vol. 45, No. 9 (1999) pp. 1530-1535.*
English Language Abstract of T. Karatsu, et al., "Determination of the Glucose in Serum by the FT-IR-ATR Method", Bunseki Kagaku, vol. 54, No. 2, Feb. 5, 2005, abstract only.
C. Petibois, et al., "Determination of Glucose in Dried Serum Samples by Fourier-Transform Infrared Spectroscopy", Clinical Chemistry, vol. 45, No. 9, 1999, pp. 1530-1535.
C. Petibois, et al., "Plasma Protein Contents Determined by Fourier-Transform Infrared Spectromety", Clinical Chemistry, vol. 47, No. 4, 2001, pp. 730-738.

* cited by examiner

*Primary Examiner* — Rebecca E Prouty
*Assistant Examiner* — Paul C Martin
(74) *Attorney, Agent, or Firm* — Baker Botts L.L.P.

(57) ABSTRACT

The objective of the present invention is to provide a method and instrument for measuring glucose concentration in blood using infrared spectroscopy. Glucose concentration in blood is measured based on an integrated value obtained by measuring an absorption spectrum that includes the wavenumber range of 1020-1040 $cm^{-1}$, and by integrating the intensity of absorption of the wavenumber range of 1020-1040 $cm^{-1}$ within the absorption spectrum. Alternatively, a glucose concentration in blood is measured based on an integrated value through measuring an absorption spectrum including the wavenumber range of 1010-1050 $cm^{-1}$; obtaining a second-derivative spectrum by calculating a second derivative of the absorption spectrum that includes the wavenumber range of 1010-1050 $cm^{-1}$ in the absorption spectrum; determining an integration range based on the second derivative spectrum; and then obtaining the integrated value by integrating the intensity of absorption based on this determined integration range.

1 Claim, 9 Drawing Sheets

(a)

(b)

METHOD FOR MEASURING GLUCOSE CONCENTRATION IN BLOOD USING INFRARED SPECTROSCOPY AND INSTRUMENT EMPLOYING IT

CROSS REFERENCE TO RELATED APPLICATIONS

This application claims priority under 35 U.S.C. 119 based upon Japanese Patent Application Serial No. 2004-223934, filed on Jul. 30, 2004. This application is a U.S. national phase application of PCT/JP2005/013660 filed on Jul. 26, 2005, claiming the above priority. The entire disclosure of the aforesaid application is applications are incorporated herein by reference.

FIELD OF THE INVENTION

The present invention relates to a method for measuring glucose concentration in blood using infrared spectroscopy, and an instrument employing it.

BACKGROUND OF THE INVENTION

As a method and instrument for measuring diabetic patients' blood sugar level, namely, glucose concentrations in blood, a method and instrument using absorptions in near-infrared regions have been known. However, they have not been used widely due to the level of their accuracy and difficulties in their measuring methods. On the other hand, a method and instrument for measuring glucose concentrations in blood using infrared spectroscopy have been proposed, which are described in Japanese Patent Laid-Open Publication No. 2003-042948 (hereafter referred to as patent document 1)

SUMMARY OF THE INVENTION

However, similar to the method and instrument for measuring glucose concentrations in blood using absorptions in near-infrared regions, the technology disclosed in the above-mentioned patent document 1 cannot adequately specify a wavenumber range that corresponds to a glucose concentration, and since it includes errors due to absorptions of other elements, its quantitative measurement accuracy is considered inadequate.

Accordingly, the objective of the present invention is to provide a method for measuring glucose levels that is capable of quantifying with high accuracy using infrared spectroscopy and a device for measuring glucose levels using the same.

In order to achieve the above-mentioned objective, the present invention has the following aspects. As a first aspect of the present invention, there is provided a method for measuring glucose concentrations in blood comprising the steps of measuring an absorption spectrum that includes the wavenumber range of 1020-1040 $cm^{-1}$, obtaining an integrated value by integrating the absorption intensity of the wavenumber range of 1020-1040 $cm^{-1}$ in the absorption spectrum, and determining the glucose concentration in blood based on the integrated value. The inventors of the present invention have reached a conclusion that among the various peaks that are attributed to glucose, peaks in the vicinity of 1030 $cm^{-1}$ are extremely useful for quantifying glucose concentrations in blood, and thus adapted 1020-1040 $cm^{-1}$ as the range for the peaks that appear in that vicinity. With this method, a glucose concentration in blood can be sufficiently quantified. In addition, in this case, it is preferable to obtain an integrated value using a two-point based method.

In addition, in this case, it is preferable to measure a glucose concentration in blood, based on the relationship between pre-obtained integrated values and glucose concentrations, and an integrated value obtained from an absorption spectrum. By the way, "the relationship between pre-obtained integrated values and glucose concentrations" means a relationship in which a glucose concentration can be found by finding its integrated value: for example, a function relationship such as an analytical curve and a data table of integrated values and corresponding glucose concentrations. However it is not limited to those, and can be other relationships as long as a glucose concentration is found by its integrated value.

In addition, as a second aspect of the present invention, there is provided a method for measuring a glucose concentration in blood comprising the steps of measuring an absorption spectrum that includes the wavenumber range of 1010-1050 $cm^{-1}$, obtaining a second-derivative spectrum by calculating the second derivative of an absorption spectrum that includes the wavenumber range of 1010-1050 $cm^{-1}$ in the absorption spectrum, determining an integration range based on the second derivative spectrum, obtaining an integrated value by integrating the absorption intensity in the integration range determined, and determining the glucose concentration in blood based on the integrated value. According to this method, even when a absorption peak near 1030 $cm^{-1}$ is somewhat off due to measurement conditions, by calculating the second derivative, an inflection point is sufficiently specified, and thus an integration range can be obtained accurately. In addition, in this case, it is more preferable to obtain the integrated value by a two points method using a straight line.

In addition, in this case, it is more preferable to obtain a glucose concentration in blood based on the relationship between pre-determined integrated values and glucose concentrations and the integrated value obtained from the absorption spectrum.

In addition, in this case, it is more preferable that the glucose concentration in blood is measured based also on the concentration of total protein in blood.

In addition, in this case, it is preferable that the glucose concentration in blood is measured based also on the intensity of absorption in the wavenumber range of 1450-1750 $cm^{-1}$.

In this aspect, if the deviation of a peak in each measurement is determined to be small, it is possible to use the wavenumber range of 1020-1040 $cm^{-1}$ in place of the wavenumber range of 1010-1050 $cm^{-1}$.

Furthermore, as a third aspect, there is provided a device for measuring a glucose concentration in blood comprising: an absorption spectrum measuring means for measuring an absorption spectrum that includes the wavenumber range of 1020-1040 $cm^{-1}$; an integration means that outputs an integrated value by integrating the intensity of absorption in the wavenumber range of 1020-1040 $cm^{-1}$ from the absorption spectrum that the absorption spectrum measuring means measures; and a concentration determination means to determine the glucose concentration in blood based on the output of the integration means. As the absorption spectrum measuring means, an instrument for measuring infrared absorption spectra falls into the category, which includes a means to generate light in the infrared region, a means to direct the light into a liquid sample, a light reception means to receive light after the absorption by the sample, and a means to calculate the absorption spectrum based on the quantity of the light received in the light reception means. In addition, the integration means, for example, may be a program that performs a peak processing based on the calculated absorption spectrum, and the concentration determination means may include a program or a table of data for obtaining a glucose concentration that corresponds to an integrated value.

Furthermore, as a fourth aspect, there is provided a device for measuring a glucose concentration in blood comprising an absorption spectrum measuring means for measuring an absorption spectrum that includes the wavenumber range of 1010-1050 $cm^{-1}$, a second-derivative spectrum calculation means to calculate a second-derivative spectrum by getting the second-derivative of the absorption spectrum that includes the wavenumber range of 1010-1050 $cm^{-1}$, an integration range calculation means to determine an integration range based on this second derivative spectrum calculated by this second-derivative spectrum calculation means, an integration means to obtain an integrated value by integrating the intensity of absorption in the absorption spectrum based on the output of this integration range calculation means; and a concentration determination means to determine the glucose concentration in blood based on the integrated value obtained by the integration means. The second derivative spectrum calculation means may be a program that calculates a second derivative based on the data of a measured absorption spectrum, and the integrated value calculation means may be a program that contains a function to determine the wavenumber of absorption which has an intensity appropriate for an integration range by referring to the intensity data in the second derivative spectrum.

As explained above, a method for measuring glucose concentration in blood using infrared spectroscopy, and the instrument using the method, which enable quantification of high accuracy are provided.

DETAILED DESCRIPTION OF THE PREFERRED EMBODIMENTS

Figure 1:
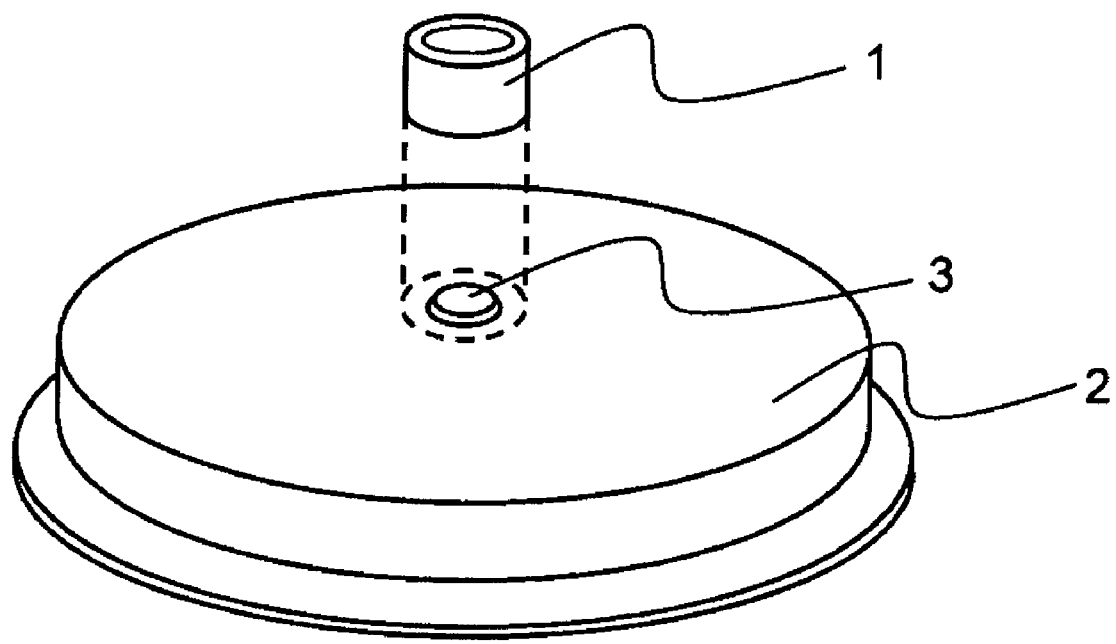
FIG. 1 is a perspective diagram which shows a sampling plate and solution holder of Example 1.

A detailed description of the preferred embodiments of the present invention is described hereafter. First of all, in the current example, collected blood is measured by infrared spectroscopy to obtain its absorption spectrum. For that, the wavenumber is required to contain the 1020-1040 $cm^{-1}$ wavenumber range, and more preferably it includes the wavenumber range of 1030±20 $cm^{-1}$ for ensuring accurate measurements. Next, a second derivative is calculated for the absorption spectrum that includes the range of 1020-1040 $cm^{-1}$ (preferably the range of 1030±20 $cm^{-1}$) to obtain a secondary absorption spectrum. After that, 2 points, in the range of 1020-1040 $cm^{-1}$ (preferably the range of 1030±20 $cm^{-1}$), are determined in this secondary absorption spectrum. Integration is performed to the original absorption spectrum using the two points based approach in the wavenumber range that correspond to those two points, and the result is set as the peak area, and then based on the integrated value the glucose concentration in the blood is evaluated.

In the current example, absorption peaks in the vicinity of 1030 $cm^{-1}$ are considered extremely useful for quantifying a glucose concentration in blood, and since two points that form the base for an integration range are obtained by taking the second derivative of an absorption spectrum, even when a target peak is off by a few $cm^{-1}$ due to various elements in each measurement, a peak area can be accurately obtained by removing this deviation. In addition, as the method for obtaining the two points that determine the integration range, it is preferable to set two peaks located on both sides of the peak that appears in the 1030 $cm^{-1}$ vicinity as the two points. However depending on the shape of the spectrum some deviations are within the allowable range.

Furthermore, the current example is extremely useful in terms of its ability for accurate measurement because it determines an integration range by obtaining a second derivative. However, if the level of measurement is such that deviations of peaks in measurement can be ignored, then it can be measured by uniformly obtaining the wavenumber range between 1020 $cm^{-1}$ and 1040 $cm^{-1}$. In this case the measurement accuracy would be sacrificed, but a measurement can be abbreviated, and thus measurements can be done quickly.

In addition, as long as the wavenumber range of 1020-1040 $cm^{-1}$ (preferably, the range of 1030±20 $cm^{-1}$) is included, the measuring of an infrared absorption spectrum that includes other ranges does not cause any problems. On the other hand, when obtaining an integrated value, it is evaluated by the wavenumber range which becomes the base, obtained by the second derivative (or the wavenumber range between 1020-1040 $cm^{-1}$). Therefore, it is not appropriate to determine the integrated value by including the other ranges (naturally, some deviations are expected to occur, thus a range that is recognized as a deviation should be tolerated).

In addition, there are cases in which measuring absorption spectra outside of the wavenumber range of 1020-1040 $cm^{-1}$ (preferably 1030±20 $cm^{-1}$ range) is more preferable for quantifying an absolute value of glucose concentration in blood. For example, since an absorption peak related to total protein in blood appears in the range of 1450 $cm^{-1}$-1750 $cm^{-1}$, by taking into account this absorption peak and the concentration of total protein, the concentration of glucose can be absolutely measured. The method for taking them into consideration will be explained later.

On the other hand, in order to realize the current example, it is preferable to make a solution holder for more accurate measurement. The configuration is shown in FIG. 1.

Figure 2:
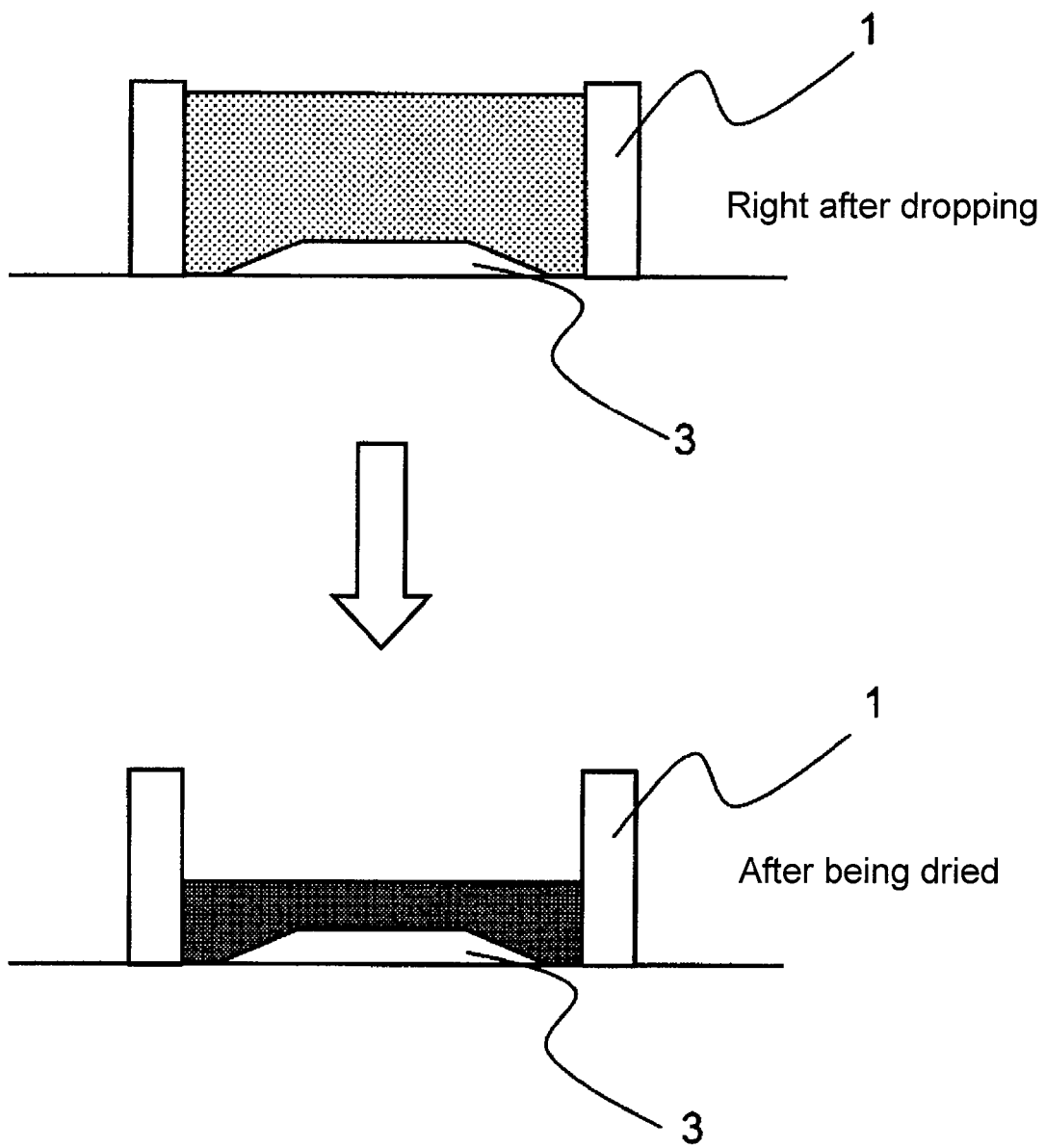
FIG. 2 is a cross-sectional drawing of the sampling plate and solution holder vicinity in Example 1.
Figure 3:
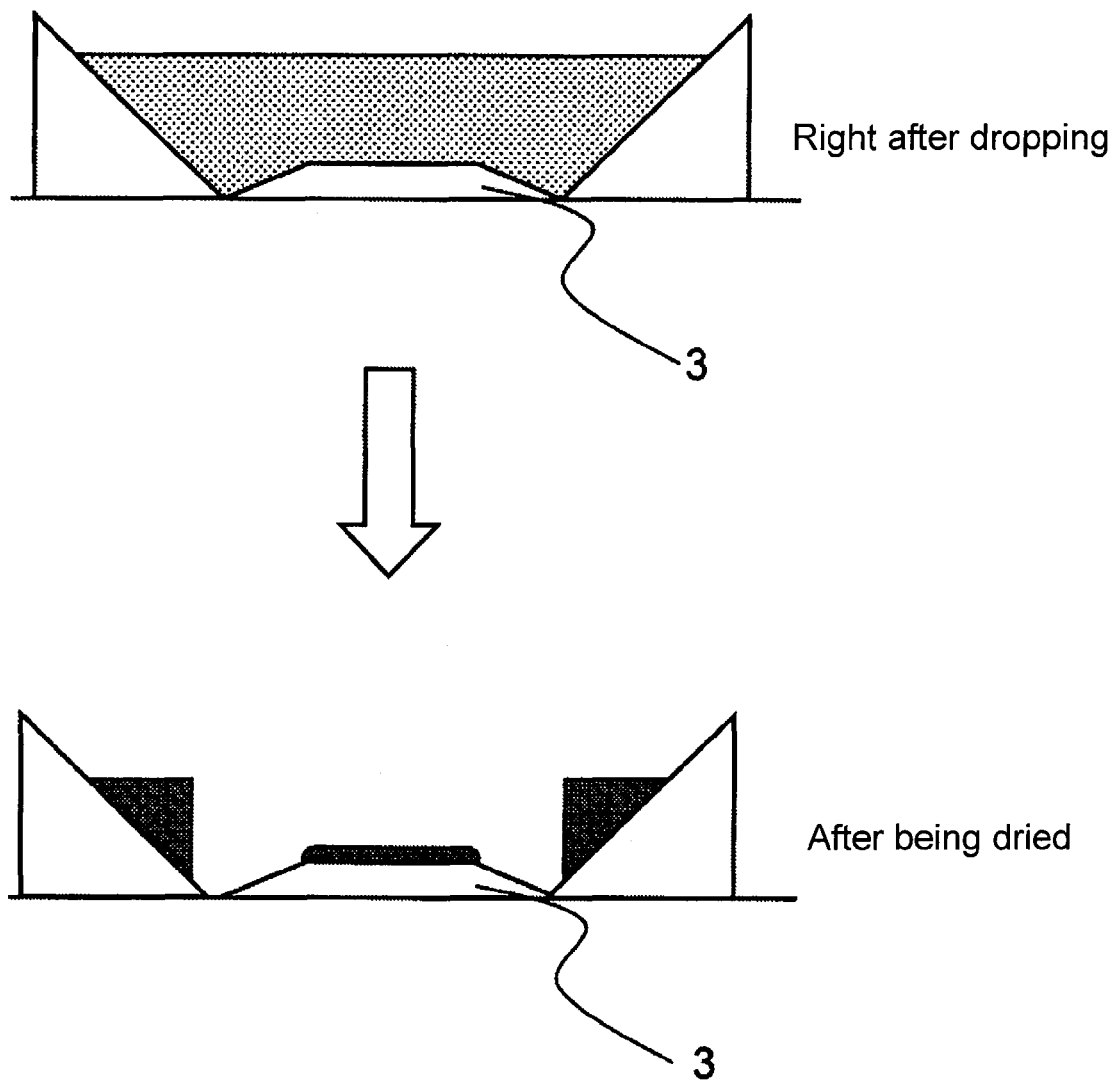
FIG. 3 is a cross-sectional drawing of a sampling plate and solution holder vicinity in a conventional example.

As shown in FIG. 1, a solution holder 1 of the current example is arranged such that it surrounds an attenuated total reflectance (hereafter referred as ATR) prism 3 on a sampling plate 2, and a concaved section is formed by the upper surface of the sampling plate 2 and the solution holder 1 to retain a liquid sample. FIG. 2 shows the cross section of the solution holder 1's vicinity and the progress after a sample is applied. The internal surface of the solution holder 1 is installed approximately perpendicular to the base, so that even when a liquid sample dries out, it can maintain a state in which the ATR prism is covered fully. On the other hand, as shown in FIG. 3, if the internal surface of the side wall is slanted, it cannot secure a sufficient amount of a dried sample on the ATR prism. The one shown in FIG. 2 has a side wall that is standing approximately perpendicular to the base, thus a sufficient amount of dried sample can be secured, and consequently an infrared absorption spectrum having a strong intensity can be obtained. "Approximately perpendicular" means that, because of the above-mentioned reason, it is preferable to be within +/−10 degrees against the sampling plate surface.

When blood is measured with infrared spectroscopy using this solution holder, it is dried under reduced-pressure. If the level of reduced pressure is too intense, bubbles occur in the blood, causing blood detachment from the ATR prism. As a result, a low infrared absorption spectrum of extremely low absorbance is created. Thus caution is needed.

EXAMPLES

In this example, blood sugar was measured from actual blood serum. This is described in detail as follows. At first, four samples are created with blood serum with a glucose concentration of 0.71 g/l (referred to as "the first blood serum" hereafter). More particularly, a sample with a 180 μl of the first blood serum and a 20 μl of distilled water (referred to as "No. 1" hereafter), a sample with a 180 μl of the first blood serum and a 20 μl of a glucose solution having a glucose concentration of 4.55 g/l (referred to as "No. 2" hereafter), a sample with a 180 μl of the first blood serum and a 20 μl of a glucose solution having a glucose concentration of 9.11 g/l (referred to as "No. 3." hereafter), and a sample with a 180 μl of the first blood serum and a 20 μl of a glucose solution having a glucose concentration of 18.21 g/l (referred as "No. 4" hereafter) are created.

In the same way, using a blood serum with a glucose concentration of 0.83 g/l (referred to as "the second blood serum" hereafter) the same glucose solutions are added to create 4 samples. Furthermore, using a blood serum with a glucose concentration of 0.71 g/l (this serum is different from the above-mentioned first serum. It is referred as "the third blood serum" hereafter) the glucose solutions are added to create 4 samples in the same way. Table 1 shows the twelve samples created.

TABLE 1

| | Base Serum | | Glucose solution added | | Glucose |
| --- | --- | --- | --- | --- | --- |
| Sample No. | Glucose concentration (g/l) | Amount collected (μl) | Glucose concentration (g/l) | Amount added (μl) | concentration after the addition |
| 1 | 0.71 | 180 | 0 (distillated water) | 20 | 0.64 |
| 2 | 0.71 | 180 | 4.55 | 20 | 1.09 |
| 3 | 0.71 | 180 | 9.11 | 20 | 1.55 |
| 4 | 0.71 | 180 | 18.21 | 20 | 2.46 |
| 5 | 0.83 | 180 | 0 (distillated water) | 20 | 0.75 |
| 6 | 0.83 | 180 | 4.55 | 20 | 1.2 |
| 7 | 0.83 | 180 | 9.11 | 20 | 1.66 |
| 8 | 0.83 | 180 | 18.21 | 20 | 2.57 |
| 9 | 0.71 | 180 | 0 (distillated water) | 20 | 0.64 |
| 10 | 0.71 | 180 | 4.55 | 20 | 1.09 |
| 11 | 0.71 | 180 | 9.11 | 20 | 1.55 |
| 12 | 0.71 | 180 | 18.21 | 20 | 2.46 |

After having made those samples, ATR type infrared absorption measurement was performed for each sample to obtain the infrared absorption spectrum. Those measurements were taken after each sample was dried in the solution holder 1 shown in FIG. 1 and FIG. 2 (outside diameter: 3.6 mm, inside diameter: 5.5 mm, height: 1.7 mm, materials: (copper with metal plated surface). Drying of the samples was done by placing a liquid state sample in the solution holder mounted on a sampling plate, then placing this sampling plate and solution holder in a desiccator where they were kept depressurized under 5 mmHg for 20 minutes. In addition, for each sample, this ATR type infrared absorption measurement is performed three times with 5 minutes intervals, and among the obtained infrared absorption spectra, the one with the largest absorption around $1000\ cm^{-1}$ was adapted as the infrared absorption spectrum of a fully dried state.

Next, for each of the absorption spectrum that was obtained as mentioned above, a second derivative was calculated to obtain a second derivative spectrum.

Figure 4A:
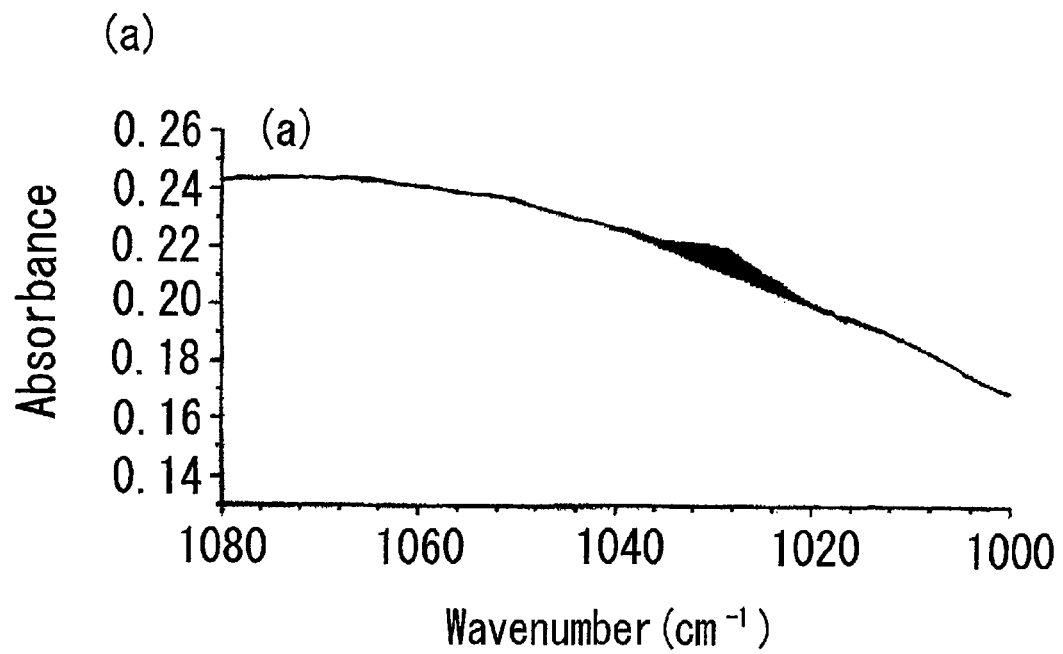
FIG. 4(a) shows an infrared absorption spectrum of Example 1.
Figure 4B:
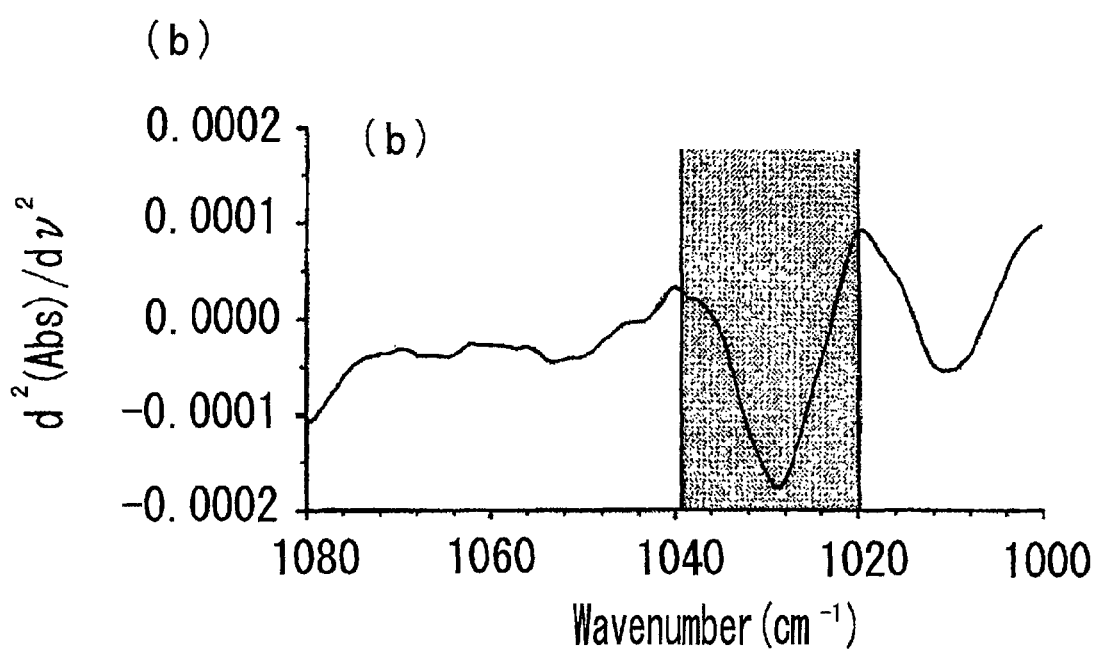
FIG. 4(b) shows a second derivative spectrum based on the infrared absorption spectrum in Example 1.

FIG. 4(a) and FIG. 4(b) show an infrared absorption spectrum and the second derivative spectrum, respectively. Based on FIG. 4(b), a downward peak near $1030\ cm^{-1}$ was recognized as the peak typical to glucose, and the distance between the two upward peaks that surround the downward peak was established as the width of the peak, that was set as 1019-1039 $cm^{-1}$. An integrated value was taken through the two point base approach for the absorption spectrum of FIG. 4 (a) for the above-mentioned range; its integrated value was set as the peak area. This operation was done for each sample, and the peak area for each sample was obtained.

Figure 5:
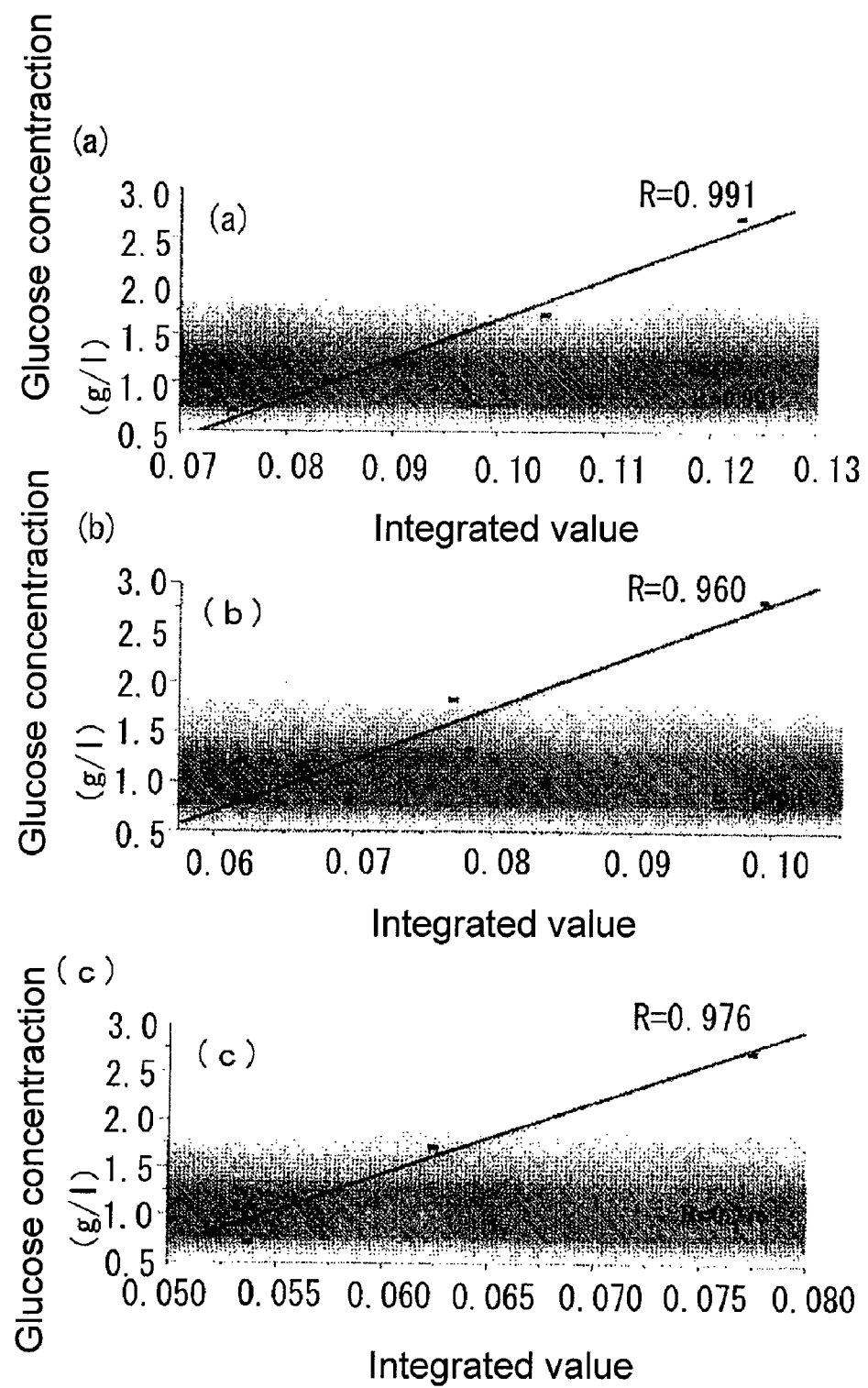
FIG. 5 shows the relationship between integrated values and glucose concentrations in respective samples in Example 1.

Next, the correlation between the peak areas and the glucose concentrations in the solutions was examined. FIG. 5 (a) shows the results of samples No. 1-4, FIG. 5 (b) shows the results of samples No. 5-8, and FIG. 5 (c) shows the results of samples No. 9-12. The line in each figure is obtained by the least-squares method.

The results obtained were: the line in FIG. 5 (a) is R=0.991, the line in FIG. 5 (b) is R=0.960, and the line in FIG. 5 (a) is R=0.976. All of them are analytical curves having high correlations, and thus it was confirmed that by obtaining an integer within this wavenumber range the correlation with a glucose concentration can be evaluated accurately. In particular this is extremely useful for the evaluation of glucose concentrations for the same person. In particular, if the relationship between glucose concentrations and peak areas is obtained before measurement in the form of an analytical curve, then, a peak area is obtained in a measurement, and a glucose concentration corresponding to the peak area can be obtained based on the analytical curve. Of course, the pre-obtained relationship can be a lineal function format as an analytical curve, but it could be as a table of data, where there is no special limitation as long as there is a correspondence between a peak area and a glucose concentration.

The analytical curves in FIG. 5 (a)-(c) are expressed by the following formulas (1), (2), and (3) respectively.

[Formula 1]

$$[\text{Concentration of glucose (g/l)}] = 37.7 \times [\text{integrated value}] - 2.27 \quad (1)$$

[Formula 2]

$$[\text{Concentration of glucose (g/l)}] = 48.0 \times [\text{integrated value}] - 2.25 \quad (2)$$

[Formula 3]

$$[\text{Concentration of glucose (g/l)}] = 69.3 \times [\text{integrated value}] - 2.87 \quad (3)$$

Figure 6:
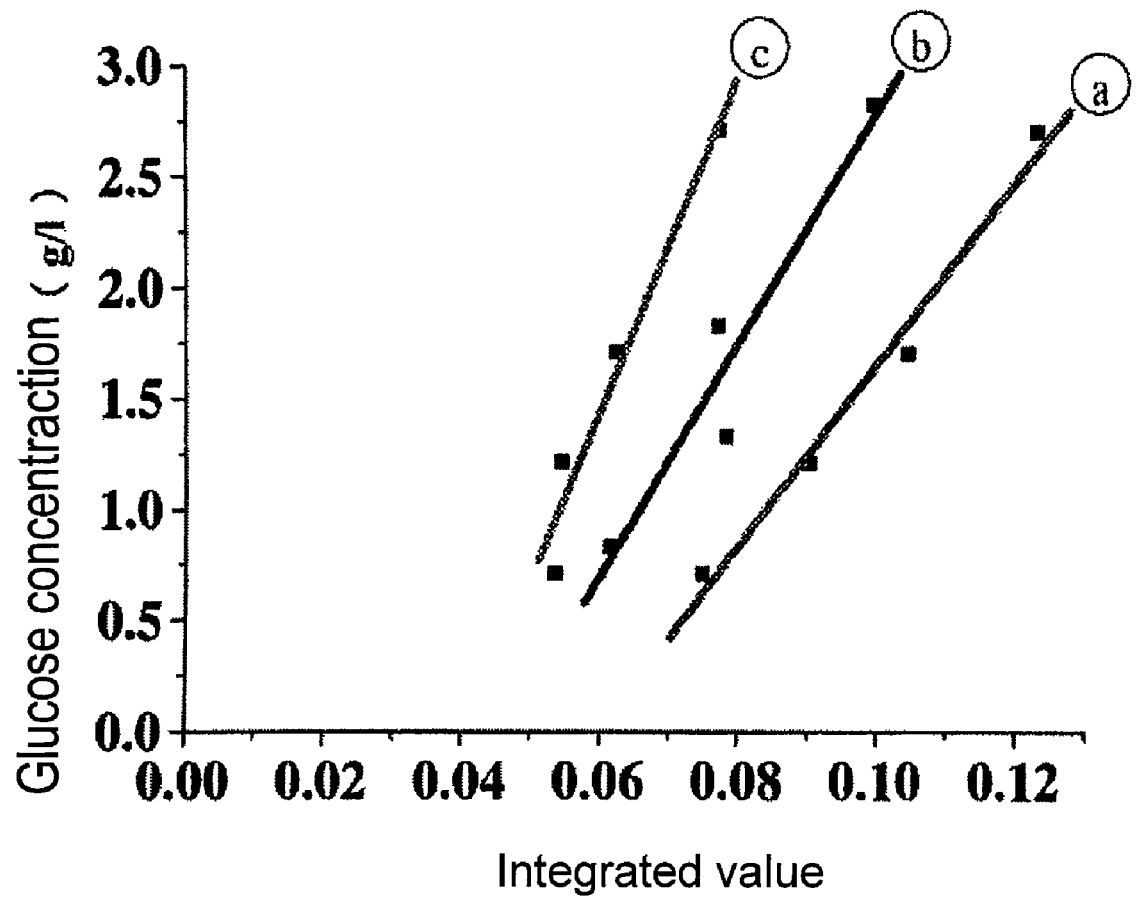
FIG. 6 shows the relationship between integrated values and glucose concentrations in respective samples in Example 1.

Next, FIGS. 5 (a)-(c) are combined into one figure, and the correlation among different blood serums was evaluated. The result is shown in FIG. 6.

Figure 7:
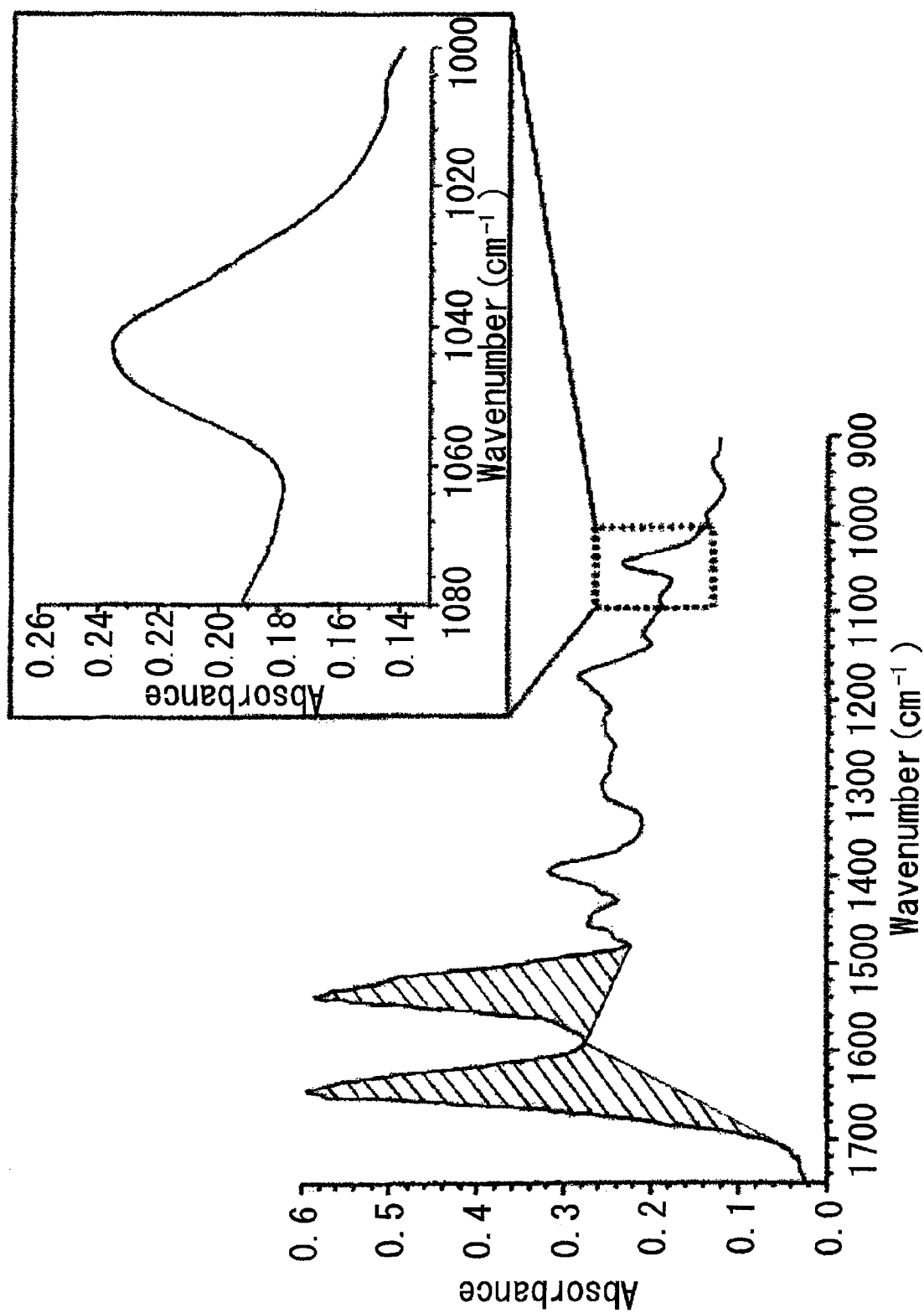
FIG. 7 shows the infrared absorption spectrum of Example 1 in the vicinity of 900-1750 $cm^{-1}$.

The samples from one blood serum show a significantly high correlation between glucose concentrations and integrated values. However, according to the result in FIG. 6, the correlation among different blood serums is weaker. Examining this result, it is considered that total protein has a great influence, in particular, it appears that albumen having a large peak centering in the vicinity of 1400 cm$^{-1}$, is considered to be influencing the results. The peaks of albumen appear in the range between 1450 cm$^{-1}$ and 1750 cm$^{-1}$ (see FIG. 7).

Thus the relativity of the three analytical curves against the total protein concentration was examined. By the way, the total protein concentrations of the samples were 38.0 g/l in No. 1-4, 64.6 g/l in No. 5-8, and 85.6 g/l in No. 9-12.

Figure 8:
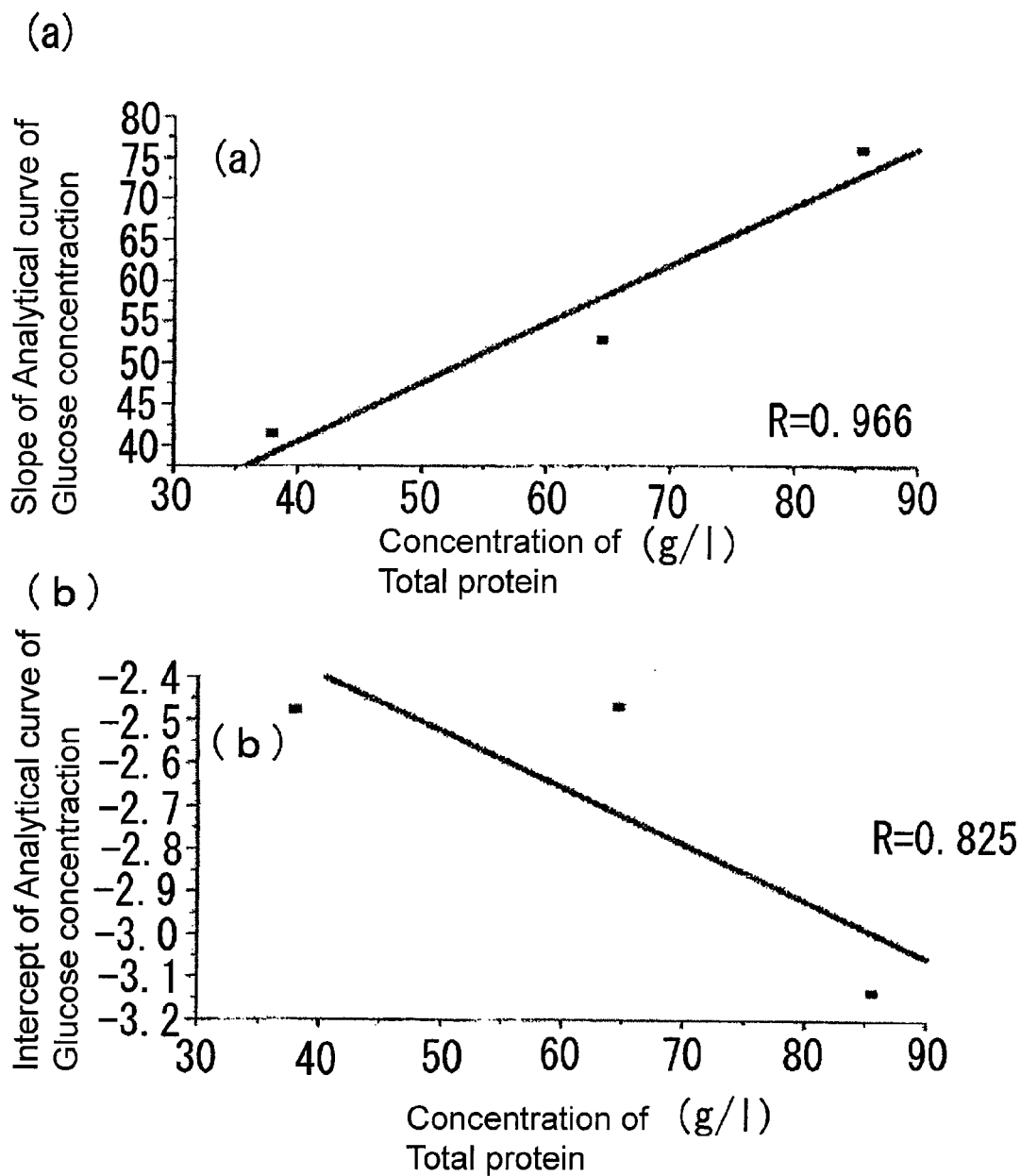
FIG. 8 shows the relationship between total protein concentrations and the analytical curves of glucose concentrations.

FIG. 8 (a) shows the relationship between the slope of each analytical curve and total protein concentrations, and FIG. 8 (b) shows the relationship between the intercept of each analytical curve and total protein concentrations. In addition, each line in the figure was obtained by a least-squares method.

As a result, an extremely good correlation of R=0.966 was obtained in FIG. 8 (a). In addition, it was R=0.807 in FIG. 8 (b). These lines were expressed with the following formulas respectively.

[Formula 4]

$$[\text{Slope of analytical curve}] = 0.653 \times [\text{Concentration of total protein (g/l)}] - 10.7 \quad (4)$$

[Formula 5]

$$[\text{Intercept of analytical curve}] = -1.21 \times 10^{-2} \times [\text{Concentration of total protein (g/l)}] - 1.70 \quad (5)$$

From the above-mentioned formulas (1) to (5), a formula for obtaining glucose concentrations was successfully obtained, having an integrated value within 1019-1039 cm$^{-1}$ and total protein concentration as a variable.

[Formula 6]

$$[\text{Glucose concentration (g/l)}] = [0.653 \times [\text{Total protein concentration (g/l)}] + 10.7] \times [\text{Integrated value}] - [1.21 \times 10^{-2} \times [\text{Total protein concentration (g/l)}] + 1.70] \quad (6)$$

As explained above, correlations in each blood serum were incorporated in the formula, thus enabling an accurate quantification of the glucose level in blood.

In order to confirm the reliability of the results in the current example, similar measurements were done using four different blood serums as additional samples.

Figure 9:
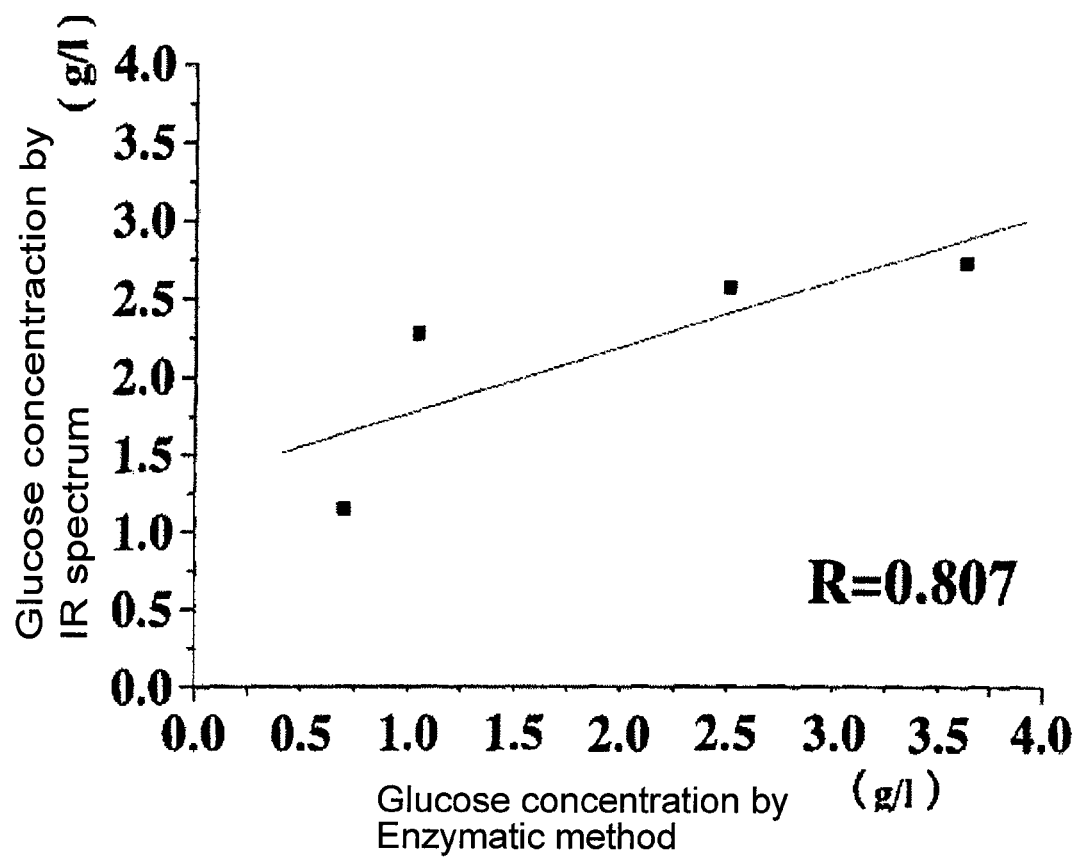
FIG. 9 shows the relationship between the glucose concentrations obtained by the measuring method of the example and the glucose concentrations obtained by an enzymatic method.

Table 2 below shows the constituents of the samples used, and FIG. 9 shows their results. Here, relationships with glucose concentrations were evaluated by an enzymatic method as the other standard for measuring glucose concentrations. No adjustment was made to these samples such as adding a glucose solution to the samples.

TABLE 2

| Sample No. | Glucose Concentration (g/l) | Total Protein Concentration (g/l) |
|---|---|---|
| 13 | 0.7 | 68 |
| 14 | 3.63 | 67 |
| 15 | 2.52 | 73 |
| 16 | 1.05 | 71 |

According to FIG. 9, a high correlation of R=0.807 is found between the results of the current example and by the enzymatic method, thus indicating that the analysis by the current example is useful.

As explained above, with the current example, an accurate quantification of glucose level was successfully realized using an infrared absorption spectrum.

In the current example, for the total protein concentrations in the samples, values that were measured beforehand were used. However, a total protein concentration can be sufficiently quantified by integrating an infrared absorption peak appearing in the range of 1450 cm$^{-1}$ to 1750 cm$^{-1}$ by the two points based method. In particular, infrared absorption peaks in this range are sufficiently large, and thus they can be easily and accurately quantified as compared to glucose concentrations. Therefore, in this case, an extremely accurate quantification can be achieved, having collected a blood serum, by measuring infrared absorption peaks near the range of 900 cm$^{-1}$ to 1400 cm$^{-1}$, and obtaining an integrated value related to glucose through second-order differentials within the 1020-1040 cm$^{-1}$ vicinity (or 1030±20 cm$^{-1}$), as well as obtaining an integrated value related total protein within the 1450 cm$^{-1}$ to 1750 cm$^{-1}$ vicinity, thus providing a useful method. In addition, the two points based method is also useful when obtaining an integrated value of the total protein.

Figure 10:
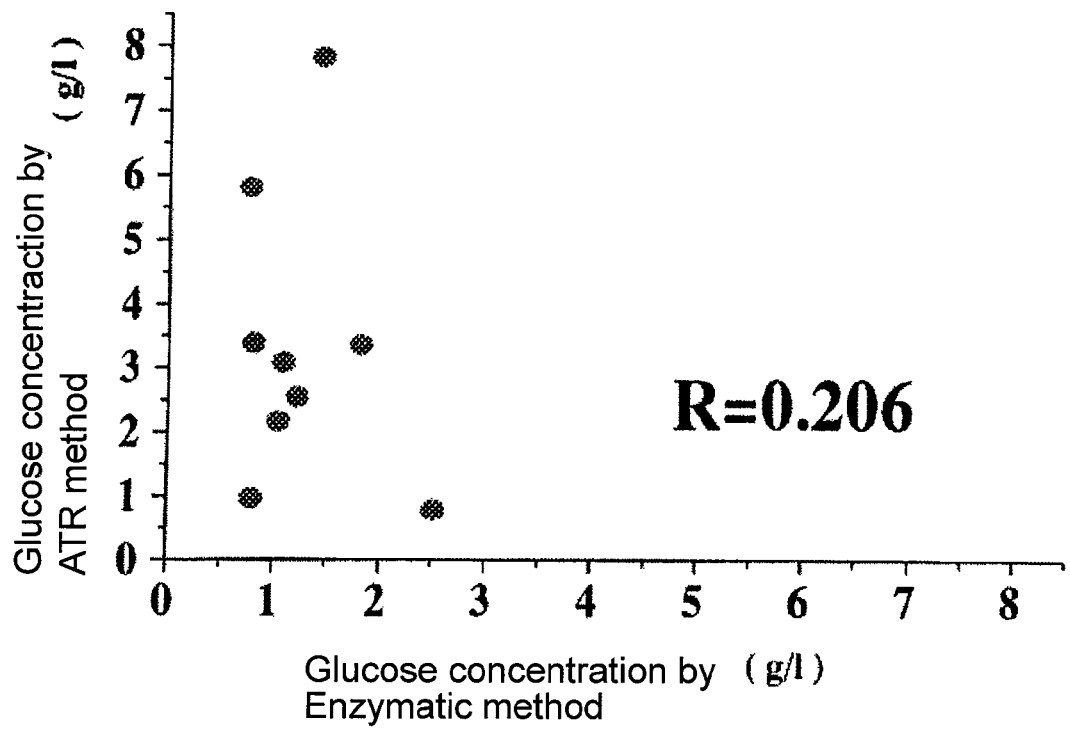
FIG. 10 shows the correlation of results by the conventional attenuated total reflectance (hereafter referred as ATR) ATR infrared spectroscopy and the enzymatic method.

(Comparison example 1) As a comparison example for verifying the effects of the present invention, measurements were taken using a common ATR type infrared spectroscopy, and compared with the results taken by the enzymatic method, which form references for glucose concentrations. The sampling was done with nine kinds of samples in all. The wavenumber range for integration is different from that of the infrared spectroscopy in Example 1.950-1140 cm$^{-1}$ was used instead. In addition, a different solution holder, which is shown in FIG. 3, was used. These results are shown in FIG. 10.

The results showed only a low correlation of R=0.206 as compared to R=0.807 of FIG. 9. Therefore, it confirmed that the measuring method of Example 1 is useful as compared with the conventional method. Moreover, in the above mentioned examples, modes in which blood is collected were shown, but as long as an absorption spectrum is obtained, it is not necessary to collect blood, and thus it can be applied to a non-invasive measurement. For example, glucose concentrations in blood can be measured by adopting an absorption spectrum measuring means, in which the above-mentioned infrared domain light enters, for example, in a forefinger of a person, while being pressed down, and wherein the light that is reflected is received. Accordingly a non-invasive measurement was tried by the method of the present invention. The actual steps taken are: first, after being wiped by alcohol dipped cotton, an index finger was pressed tightly to the ATR prism, and then a measurement similar to the one using blood serum was started. After the completion of integration, a similar second derivative spectrum was obtained. As a result, an absorption band that is characteristic to glucose was successfully specified. In other words, it was apparent that a glucose concentration could be determined from the area of this absorption band by the same process used for blood serum. As for the time for measurement, a measurement was completed in one minute which is extremely short. Therefore, the result of this experiment confirms that the measuring of blood sugar by the attenuated total reflection infrared spectroscopy of this example can be applied to non-invasive measurements.

What is claimed is:

1. A method for measuring a glucose concentration in blood, comprising the steps of:

measuring an absorption spectrum that includes a wavenumber range of 1020-1040 $cm^{-1}$ by pressing a forefinger to an ATR prism and receiving the reflected light by said forefinger;

obtaining a second derivative spectrum by calculating the second derivative of said absorption spectrum for the wavenumber range 1020-1040 $cm^{-1}$;

determining, based on said second derivative spectrum, two peak points to be used as bases for an integration range, said two peak points being two upward peaks that surround a downward peak in the wavenumber range 1020-1040 $cm^{-1}$ of said second derivative spectrum;

obtaining an integrated value by integrating the absorption intensity in said absorption spectrum using said integration range that corresponds to said determined two peak points; and determining the glucose concentration in blood based on a relationship between pre-obtained integrated values and glucose concentrations, and said integrated value obtained from said absorption spectrum.

* * * * *